United States Patent
Hishida (10) Patent No.: US 10,433,805 B2
(45) Date of Patent: Oct. 8, 2019

(54) X-RAY IMAGING APPARATUS FOR ROUNDS

(71) Applicant: Shimadzu Corporation, Kyoto (JP)

(72) Inventor: Norimasa Hishida, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 230 days.

(21) Appl. No.: 15/507,462

(22) PCT Filed: Sep. 3, 2014

(86) PCT No.: PCT/JP2014/073151
§ 371 (c)(1),
(2) Date: Feb. 28, 2017

(87) PCT Pub. No.: WO2016/035160
PCT Pub. Date: Mar. 10, 2016

(65) Prior Publication Data
US 2017/0281116 A1    Oct. 5, 2017

(51) Int. Cl.
*H05G 1/10*    (2006.01)
*A61B 6/00*    (2006.01)
(Continued)

(52) U.S. Cl.
CPC .................. *A61B 6/56* (2013.01); *A61B 6/06* (2013.01); *A61B 6/4405* (2013.01)

(58) Field of Classification Search
CPC ........... A61B 6/06; A61B 6/4405; A61B 6/56; A61B 6/4494; A61B 6/4411;
(Continued)

(56) References Cited

U.S. PATENT DOCUMENTS 8,956,045 B2 * 2/2015 Tajima ................. A61B 6/4283
378/145
2006/0108986 A1    5/2006 Funabashi
(Continued)

FOREIGN PATENT DOCUMENTS

JP    H2-276427 A    11/1990
JP    2000-60833 A    2/2000
(Continued)

OTHER PUBLICATIONS

International Search Report dated Jan. 6, 2015 from corresponding International Application No. PCT/JP2014/073151; 4 pgs.

*Primary Examiner* — Irakli Kiknadze
(74) *Attorney, Agent, or Firm* — Maier & Maier, PLLC (57) ABSTRACT

This X-ray imaging apparatus for rounds includes inside a cart a battery, a charging circuit adapted to limit charging current flowing through the battery, and a control circuit, in which the control circuit includes: a power supply voltage detecting part adapted to detect power supply voltage supplied from an external power supply; a charged voltage detecting part adapted to detect the charged voltage of the battery; a charging current detecting part adapted to detect charging current at the time when the battery is charged; and a charging current value control part adapted to, depending on a variation in the power supply voltage detected by the power supply voltage detecting part, control a charging current value set for the charging circuit.

2 Claims, 5 Drawing Sheets

(51) Int. Cl.
*A61B 6/06* (2006.01)
*G21K 5/10* (2006.01)

(58) Field of Classification Search
CPC ... A61B 6/4423; A61B 6/4233; A61B 6/4283; A61B 6/4007; A61B 6/4291; A61B 6/4452; A61B 6/542; A61B 6/00; A61B 6/548; A61B 6/547; A61B 6/4208; A61B 6/545; A61B 6/585; A61B 6/54; A61B 2560/0214; A61B 2560/0456; A61B 6/105; A61B 6/4266; A61B 6/467; A61B 6/586; A61B 6/0478; A61G 13/107; H05G 1/10; H05G 1/32; H05G 1/12; H05G 1/34; H05G 1/54; H05G 1/26; H05G 1/30; H05G 1/08; H05G 1/20; H05G 1/265; H05G 1/56; H05G 6/56; G03B 42/02; G03B 42/04; G03B 42/045; H02J 1/102; H02J 1/108; H02J 9/061; H02J 2007/0059

USPC .............................. 378/101–107, 62
See application file for complete search history.

(56) References Cited

U.S. PATENT DOCUMENTS

| 2011/0261928 | A1* | 10/2011 | Ohta ........................ A61B 6/00 378/62 |
| 2013/0223596 | A1* | 8/2013 | Kojima ................ A61B 6/4405 378/102 |
| 2014/0016747 | A1* | 1/2014 | Watanabe ................ A61B 6/56 378/62 |

FOREIGN PATENT DOCUMENTS

| JP | 2006-129619 A | 5/2006 |
| JP | 2008-61944 A | 3/2008 |
| JP | 2010-172158 A | 8/2010 |
| WO | 2012/67171 A1 | 5/2012 |

* cited by examiner

PRIOR ART

FIG.6

X-RAY IMAGING APPARATUS FOR ROUNDS

TECHNICAL FIELD

The present invention relates to an X-ray imaging apparatus for rounds including a buttery power supply.

BACKGROUND ART

An X-ray imaging apparatus for rounds includes a cart having wheels in order to move among hospital rooms, and has a configuration adapted to irradiate a subject with X-rays that are emitted from an X-ray tube supported by a supporting member and of which the irradiation field is restricted by a collimator, and detect X-rays having passed through the subject by an X-ray detector such as a flat panel detector or an image intensifier (I.I.). Also, such an X-ray imaging apparatus for rounds is mounted with a battery in the cart in order to make it possible to perform X-ray imaging in an unspecified place including the case where no external power supply is provided (see Patent Literature 1 and Patent Literature 2).

Such a battery is a supply source of electric power for driving the wheels in order to move the X-ray imaging apparatus for rounds and electric power for emitting the X-rays from the X-ray tube. In addition, the electric power is preliminarily charged in the battery from an external power supply through a power supply cord and a charging circuit.

The charging circuit incorporates a charging current control transistor, and it is known that at the time of charging, the charging current control transistor produces heat. For this reason, for the purpose of reducing the temperature rise of the charging current control transistor, there is proposed a charging device adapted to, depending on the temperature of a charging current control transistor, be able to change a charging current value or a charging voltage value at the time of charging set for a charging circuit depending on a battery charging method (see Patent Literature 3).

Meanwhile, it is known that when supply voltage from an external power supply for charging a battery varies in excess of a predetermined voltage variation range, the variation interrupts the stable action of an apparatus. For this reason, for the X-ray imaging apparatus for rounds, an allowable voltage variation range is set in order to prevent the failure of the apparatus caused by a variation in supply voltage. In addition, the X-ray imaging apparatus for rounds includes a safety mechanism that when the supply voltage varies in excess of the set voltage variation range, detects the variation as an error and stops power supply from an external power supply.

Figure 5:
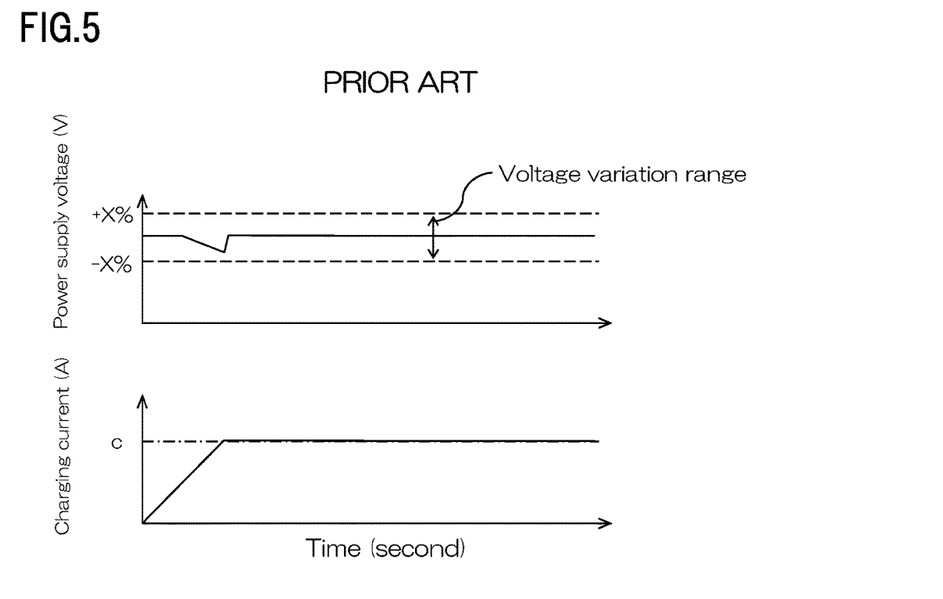
FIG. 5 is a graph explaining the relationship between external power supply voltage and charging current immediately after the start of charging in a conventional X-ray imaging apparatus for rounds.
Figure 6:
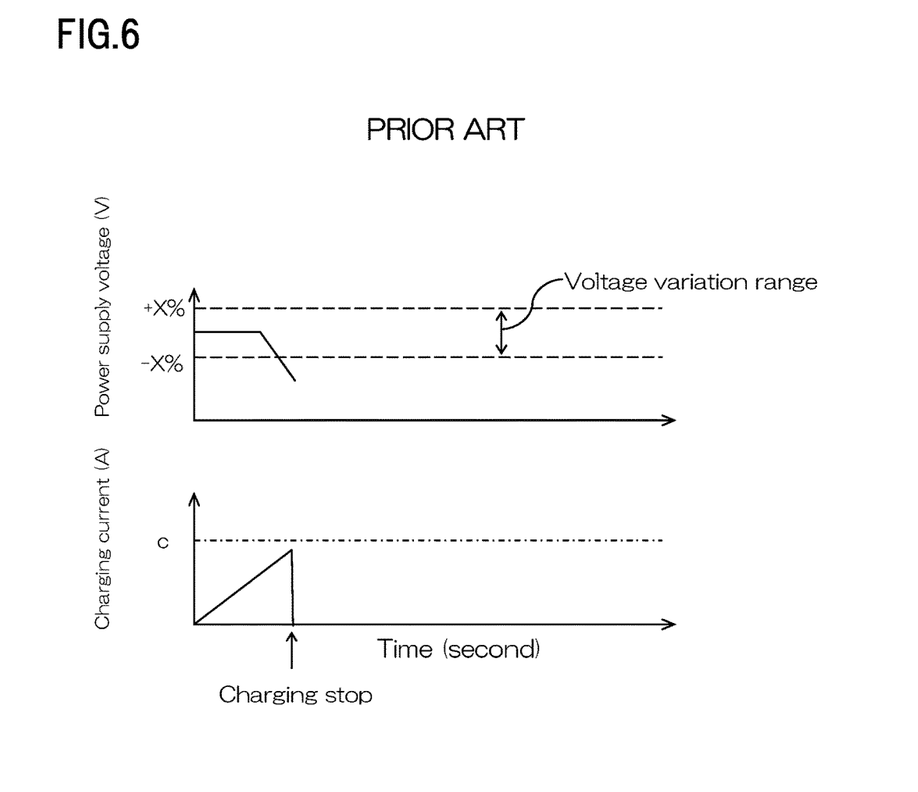
FIG. 6 is a graph explaining the relationship between external power supply voltage and the charging current immediately after the start of the charging in the conventional X-ray imaging apparatus for rounds.

FIG. 5 and FIG. 6 are graphs explaining the relationship between a variation in voltage and charging current immediately after the start of charging of a battery in a conventional X-ray imaging apparatus for rounds. In FIG. 5 and FIG. 6, the upper graphs illustrate the variations in the voltage (V) of an external power supply, and the lower graphs illustrate variations in the charging current (A). In addition, the horizontal axes of the graphs represent time (second). Note that the graphs illustrate cases when charging a lead-acid battery at a constant current.

In the conventional X-ray imaging apparatus for rounds, as the external power supply for charging the battery, a commercial power supply of which a variation in supply voltage is controlled to be within a predetermined range (e.g., a voltage variation range with respect to a standard voltage is ±10%) is assumed. For this reason, a voltage variation range ±X % (indicated by dashed lines in the graphs) allowable by the X-ray imaging apparatus for rounds is set to, for example, ±10 to 15%. In addition, the battery charging is adapted to be started, regardless of the variation in the power supply voltage, at a constant charging current value set for a charging circuit. Immediately after connecting the X-ray imaging apparatus for rounds to the external power supply, inrush current flows to temporarily cause a voltage drop. Unless such a temporal voltage drop exceeds the voltage variation range ±X %, as illustrated in FIG. 5, the charging is continuously performed at the constant charging current value c.

CITATION LIST

Patent Literature

Patent Literature 1: JP-A2008-61944
Patent Literature 2: JP-A2000-60833
Patent Literature 3: JP-A2010-172158

SUMMARY OF INVENTION

Technical Problem

However, depending on countries and regions, a variation in the voltage of a commercial power supply supplied by a power company or the like may be larger than the voltage variation range allowable by the X-ray imaging apparatus for rounds. In the case where the variation in the voltage of the external power supply is larger than the voltage variation range allowable by the X-ray imaging apparatus for rounds, the safety mechanism on the side of the X-ray imaging apparatus for rounds is activated to stop charging the battery.

Also, when using the X-ray imaging apparatus for rounds in a state where power supply from a commercial power supply is lost due to natural disaster or the like, or when using the X-ray imaging apparatus for rounds in a region where power supply equipment such as a commercial power supply is absent, electric power for charging the battery must be ensured from a power generating device called a private power generator.

However, when the capacity of the power generating device is smaller than that in power supply specifications prescribed for the X-ray imaging apparatus for rounds, connecting the X-ray imaging apparatus for rounds to the power generating device results in a significant reduction in supply voltage from the power generating device because of the insufficient capacity of the power generating device. When such a voltage drop is larger than the voltage variation range allowable by the X-ray imaging apparatus for rounds, as illustrated in FIG. 6, the safety mechanism on the side of the X-ray imaging apparatus for rounds is activated before the charging current reaches the set current value c (indicated by a dashed-dotted line in graphs), and therefore it becomes impossible to charge the battery. In addition, for the charging circuit of the conventional X-ray imaging apparatus for rounds, a current value corresponding to ¹⁄₁₀ capacity of the rated capacity of the lead-acid battery is set as the current value c.

Further, the power generating device includes a safety mechanism adapted to detect an overload to stop outputting the electric power, and therefore when connected with the X-ray imaging apparatus for rounds, the power generating device side may detect an overload to stop outputting the electric power from the power generating device. In such a case as well, it is impossible to charge the battery.

In the case where it is impossible to charge the battery, electric power necessary for X-ray imaging cannot be stored in the battery. For this reason, when necessary, X-ray imaging cannot be performed, and patient treatment and/or the like may be affected.

The present invention is made in order to solve the above-described problem, and intends to provide an X-ray imaging apparatus for rounds capable of charging a battery even when supply voltage from an external power supply is unstable.

Solution to Problem

A first aspect of the present invention includes: an apparatus main body mounted with a battery; an X-ray tube supported by the apparatus main body via a supporting member; and an X-ray detector adapted to detect an X-ray that has been emitted from the X-ray tube and passed through a subject, in which the battery serves as a power supply, and includes a control circuit having: a voltage detecting part adapted to detect voltage that is inputted from an external power supply to a charging circuit when charging the battery; and a charging current control part adapted to, during a certain time after a start of the charging of the battery, change a setting value of charging current for the battery depending on a drop rate of a value of the voltage detected by the voltage detecting part.

A second aspect of the present invention is the first aspect according to the present invention in which the charging current control part increases the setting value of the charging current in a multistep manner or at a predetermined gradient during the certain time after the start of the charging of the battery.

Advantageous Effects of Invention

According to the first aspect of the present invention, by including the control circuit having; the voltage detecting part adapted to detect the voltage that is inputted from the external power supply to the charging circuit when charging the battery; and the charging current control part adapted to change the setting value of the charging current for the battery depending on the drop rate of the value of the voltage detected by the voltage detecting part, a charging current value can be changed so as to prevent the occurrence of a voltage drop exceeding a voltage variation range set for an X-ray imaging apparatus for rounds, and therefore even when charging the battery from an unstable commercial power supply of which a variation in supply voltage is large or a private power generator having small capacity, the stop of the charging of the battery can be avoided to continue the charging of the battery.

According to the second aspect of the present invention, since the charging current control part increases the setting value of the charging current in the multistep manner or at the predetermined gradient during the certain time after the start of the charging of the battery, the maximum current value not causing the voltage drop exceeding the voltage variation range can be set as the charging current value.

DESCRIPTION OF EMBODIMENTS

Figure 1:
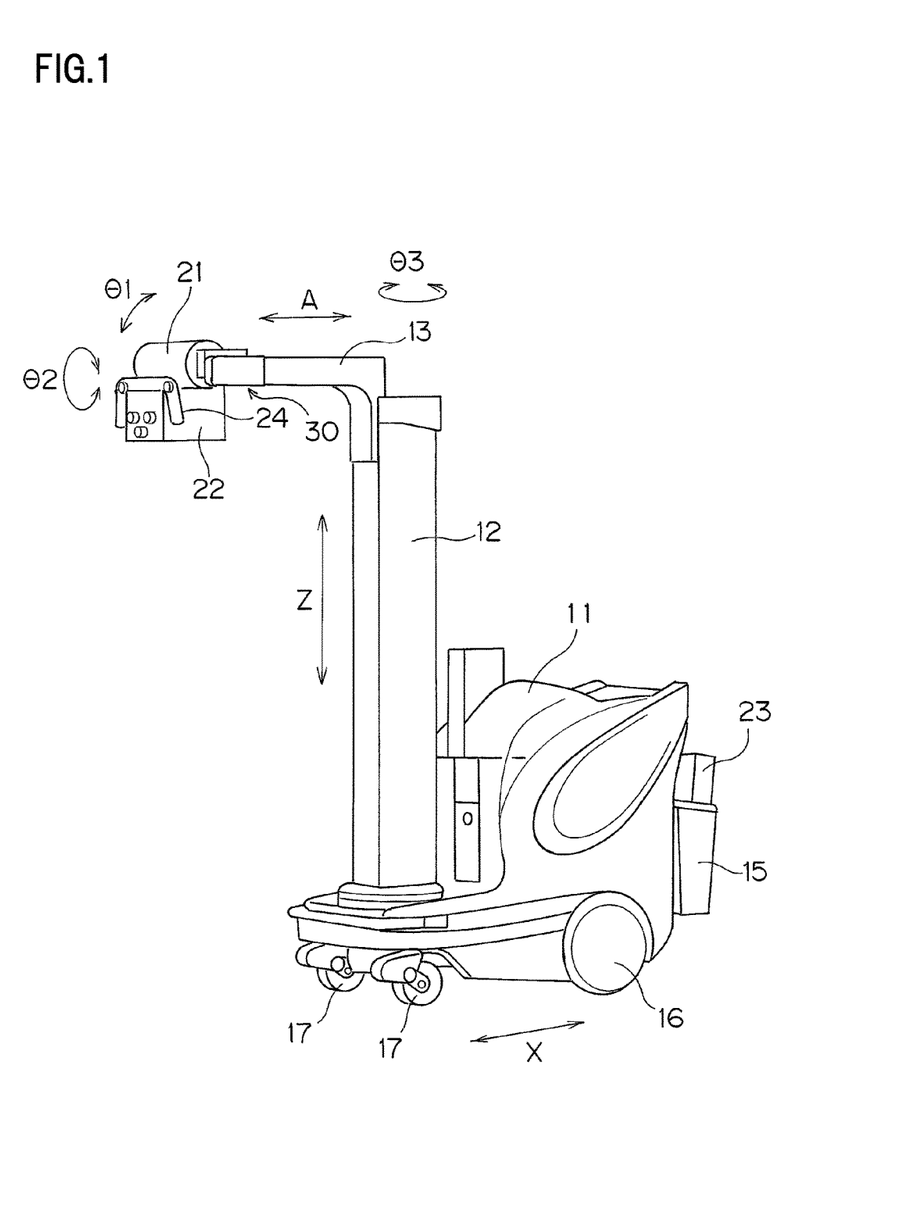
FIG. 1 is a perspective view of an X-ray imaging apparatus for rounds according to the present invention.
Figure 2:
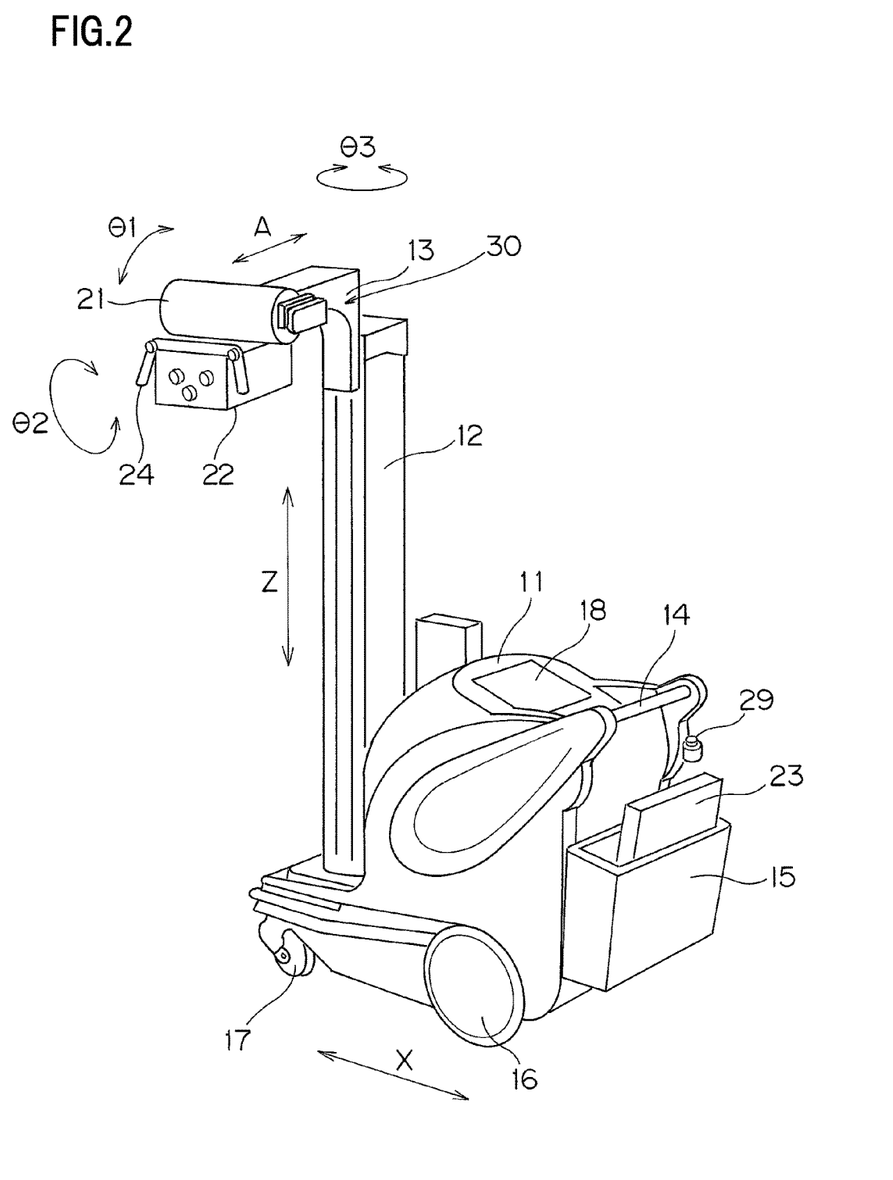
FIG. 2 is a perspective view of the X-ray imaging apparatus for rounds according to the present invention.

In the following, an embodiment of the present invention will be described on the basis of drawings. FIG. 1 and FIG. 2 are perspective views of an X-ray imaging apparatus for rounds according to the present invention.

The X-ray imaging apparatus for rounds is one that moves among multiple hospital rooms to perform X-ray imaging in each of the hospital rooms, and includes: a support post 12 disposed on a cart 11; an arm 13 disposed movably up and down along the support post 12; an X-ray tube 21 disposed at the fore end of the arm 13; a collimator 22 disposed below the X-ray tube 21; an X-ray detector 23 for detecting X-rays having been emitted from the X-ray tube 21 and passed through a subject, such as a flat panel detector; a switch 29 for emitting X-rays from the X-ray tube 21 to start X-ray imaging; and a containing part 15 for containing the X-ray detector 23. In addition, the X-ray imaging apparatus for rounds includes: a pair of left and right front wheels 17 as wheels for changing a direction; a pair of left and right rear wheels 16 as wheels to be driven by the below-described motor 46; an operation handle 14 for operating the traveling direction of the cart 11; and a touch panel 18 functioning as a display part and an operation part.

The collimator 22 is annexed with a handle 24 that is used when integrally moving the X-ray tube 21 and the collimator 22. Also, the X-ray tube 21 is supported by the arm 13 via a holding part 30.

As illustrated in FIG. 1 and FIG. 2, the X-ray tube 21 and the collimator 22 attached to the X-ray tube 21 are adapted to be swingable in a θ1 direction around a shaft facing in a direction orthogonal to an extending direction of the arm 13 and in a θ2 direction around a shaft facing in the extending direction of the arm 13. Also, as illustrated in FIG. 1 and FIG. 2, the arm 13 revolves in a θ3 direction around the support post 12, and thereby the X-ray tube 21 and the collimator 22 are adapted to be movable in the horizontal direction. Further, as illustrated in FIG. 1 and FIG. 2, the arm 13 telescopes in an A direction, and thereby the X-ray tube 21 and the collimator 22 are adapted to be movable in the horizontal direction. Still further, as illustrated in FIG. 1 and FIG. 2, the arm 13 moves up and down in a Z direction along the support post 12, and thereby the X-ray tube 21 and the collimator 22 are adapted to be movable in the vertical direction.

Note that FIG. 1 illustrates a state where the extending direction of the arm 13, i.e., the direction indicated by the arrow A in FIG. 1, in which the X-ray tube 21 and the collimator 22 moves together with the arm 13, and a direction indicated by an arrow X in FIG. 1, in which the cart 11 moves to the front are parallel, and FIG. 2 illustrates a state where the extending direction of the arm 13, i.e., the direction indicated by the arrow A in FIG. 2, in which the X-ray tube 21 and the collimator 22 moves together with the arm 13, and the direction indicated by the arrow X in FIG. 2, in which the cart 11 moves to the front are orthogonal directions.

Figure 3:
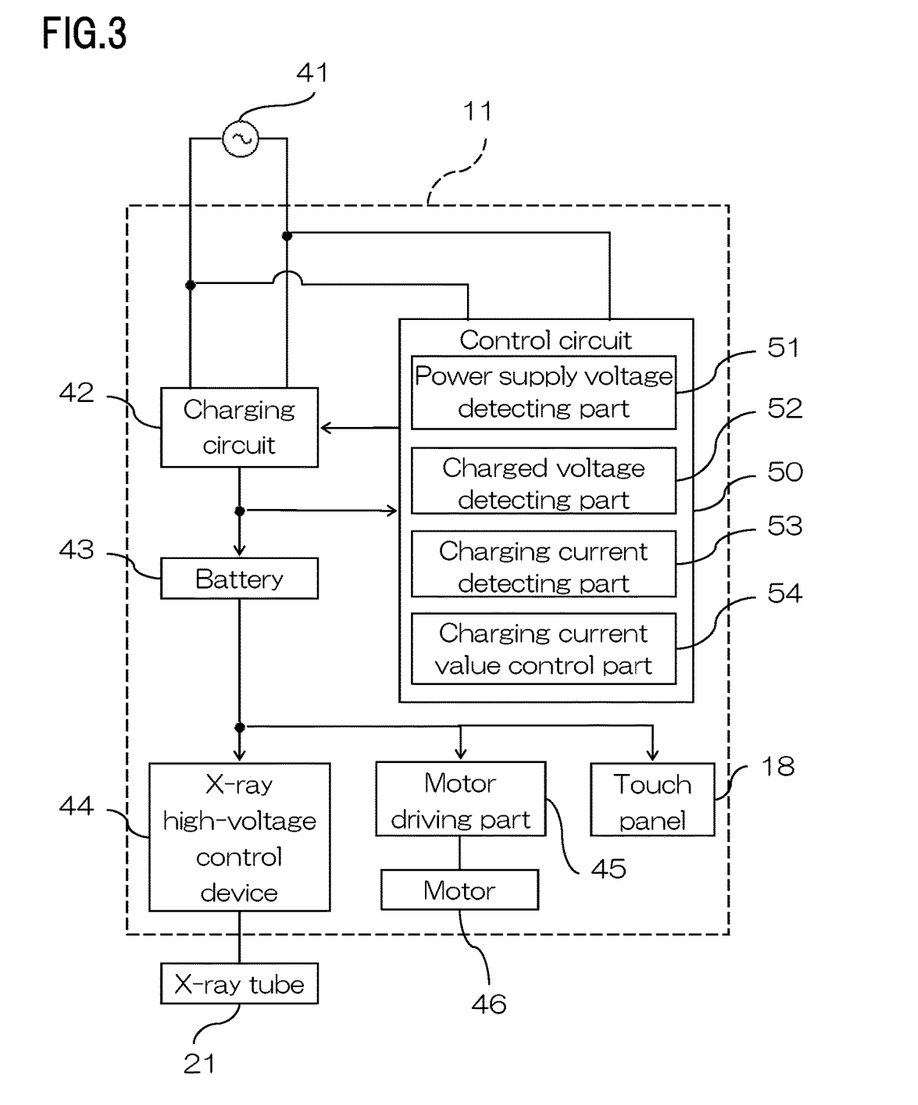
FIG. 3 is a block diagram illustrating the main electrical configuration of the X-ray imaging apparatus for rounds according to the present invention.

FIG. 3 is a block diagram illustrating the main electrical configuration of the X-ray imaging apparatus for rounds according to the present invention.

The X-ray imaging apparatus for rounds includes a battery 43, a charging circuit 42 adapted to limit charging current flowing through the battery 43, and a control circuit 50 inside the cart 11. The battery 43 is connected to an X-ray high-voltage control device 44 adapted to control various conditions at the time of the emission of the X-rays from the X-ray tube 21, such as tube current/tube voltage and an irradiation time, a motor driving part 45 adapted to control the driving of the motor 46 for driving the rear wheels 16, and the touch panel 18 adapted to display various pieces of information necessary for an X-ray imaging image and X-ray imaging, and supplies electric power necessary for the actions of them. As the battery 43, for example, a lead-acid battery is used.

The control circuit 50 includes, as a functional configuration, a power supply voltage detecting part 51 adapted to detect power supply voltage supplied from an external power supply 41; a charged voltage detecting part 52 adapted to detect the charged voltage of the battery 43; a charging current detecting part 53 adapted to detect the charging current at the time of charging the battery 43; and a charging current value control part 54 adapted to control a charging current value that is set for the charging circuit 42 depending a variation in the power supply voltage detected by the power supply voltage detecting part 51.

Figure 4:
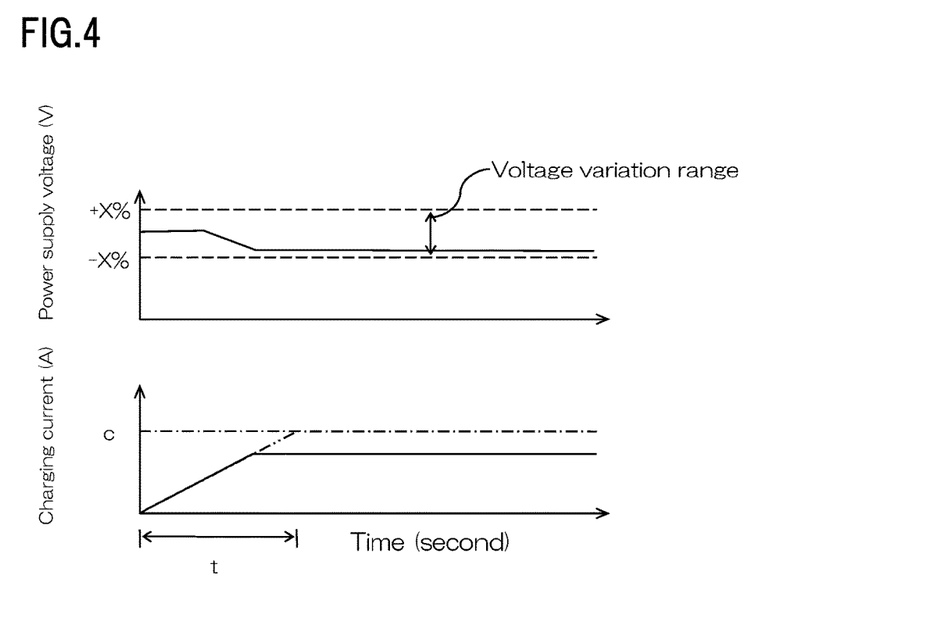
FIG. 4 is a graph explaining the relationship between external power supply voltage and charging current immediately after the start of charging in the X-ray imaging apparatus for rounds according to the present invention.

The setting of the charging current value for the charging circuit 42 at the time of charging the battery 43 in the X-ray imaging apparatus for rounds having the configuration as described above will be described in more detail. FIG. 4 is a graph explaining the relationship between the external power supply voltage and the charging current immediately after the start of the charging in the X-ray imaging apparatus for rounds according to the present invention. The upper graph in FIG. 4 illustrates the variation in the voltage (V) of the external power supply, and the lower graph illustrates a variation in the charging current (A). In addition, the horizontal axes of the graphs represent time (second).

The rapid voltage drop of the supply voltage from the external power supply 41 side occurs, in particular, because the X-ray imaging apparatus for rounds is connected and consequently an excessive load is placed on the external power supply 41. Usually, when charging the lead-acid battery at a constant current, a predetermined value (e.g., a current value corresponding to 1/10 capacity of the rated capacity of the lead-acid battery) is set for the charging circuit 42 as the charging current value. In addition, as previously described with reference to FIG. 5 and FIG. 6, immediately after connecting the X-ray imaging apparatus for rounds to the external power supply 41, partly due to the effect of inrush current, the charging current flowing through the battery 43 via the charging circuit 42 reaches the set charging current value in a few seconds. When the external power supply 41 at this time is a private power generator having small capacity or an unstable commercial power supply that supplies electric power at lower voltage than a standard voltage, the power supply voltage reduces in excess of the voltage variation range allowable by the X-ray imaging apparatus for rounds, and consequently the charging of the lead-acid battery stops.

In the X-ray imaging apparatus for rounds according to the present invention, the charging current value at the time of starting the charging of the battery 43 set for the charging circuit 42 is adapted to be changed without being set to a predetermined value as in the usual manner. A setting value change such as setting an initial value to 0 A (amperes) and increasing the setting value by 5 A every two seconds, a setting value change adapted to preset the minimum value, the maximum value, and a time t (second) required to reach the maximum value from the minimum value and change the charging current value at a predetermined gradient, or another setting value change is made.

FIG. 4 illustrates, as an example, variable charging current control (a dashed-two dotted line in the lower graph) adapted to increase the setting value of the charging current from the minimum value 0 A to the maximum value c A at a predetermined gradient during a certain time t after the start of the charging. Note that in the example of FIG. 4, as the maximum value c, the current value that is usually set for the charging circuit 42 as the charging current value at the time of starting the charging and corresponds to 1/10 capacity of the rated capacity of the battery 43 is employed. Also, in consideration of the fact that the time required to reach the usual predetermined charging current value (the current value corresponding to the 1/10 capacity of the rated capacity) after the X-ray imaging apparatus for rounds has been connected to the external power supply 41 is a few seconds, the certain time t is set to a time of ten to a few ten seconds that is approximately two to five times longer than a few seconds. In other words, the certain time t is set such that speed before reaching the charging current value before reaching which the charging is continued becomes slower than usual.

In the X-ray imaging apparatus for rounds according to the present invention, since the power supply voltage detecting part 51 can notify the variation in the power supply voltage, the charging current value set for the charging circuit 42 is changed depending on the drop rate of the power supply voltage value. That is, as indicated by solid lines in FIG. 4, when in the process of increasing the charging current value set for the charging circuit 42 stepwise or at a predetermined gradient, the voltage value detected by the power supply voltage detecting part 51 drops close to the lower limit value of the voltage variation range allowable by the X-ray imaging apparatus for rounds, the increase in the charging current value is stopped.

When stopping the increase in the charging current value as described, since the current does not flow more than before, the voltage drop stops, and the power supply voltage can be prevented from falling below the lower limit value of the voltage variation range allowable by the X-ray imaging apparatus for rounds. As a result, the charging of the battery 43 can be continued.

As the drop rate of the power supply voltage serving as a criterion for stopping the increase in the charging current value in the charging current value control part 54, a drop rate 1 to 2% smaller than the maximum voltage variation drop rate allowable by the X-ray imaging apparatus for rounds is preferable. For example, when the voltage variation range allowable by the X-ray imaging apparatus for rounds is set to ±10% of the standard voltage, at the time when the voltage value from the external power supply 41 detected by the power supply detecting part 51 reaches a value 8 to 9% lower than the standard voltage, the charging current value control part 54 performs control to stop the increase in the charging current value set for the charging circuit 42. Alternatively, it may be adapted to increase the charging current value set for the charging circuit 42 when the voltage value rises.

In the above-described embodiment, the case of a constant current charging method has been described; however, when charging the battery 43 using another charging method as well, the change in the charging current value by the charging current value control part 54 can be made depending on the voltage value detected by the power supply voltage detecting part 51. That is, the voltage drop immediately after the start of the charging is a phenomenon occurring also when charging the battery 43 using another charging method such as a constant current/constant voltage charging method or a multistep constant current charging method. In the present invention, since during the certain time after the start of the charging of the battery 43, the charging current value set for the charging circuit 42 is changed to prevent current causing a voltage drop exceeding the voltage variation range from flowing through a battery charging system, subsequent charging of the battery 43 can be continued. Accordingly, when charging the battery 43 using another charging method as well, the above-described change in the charging current value by the charging current value control part 54 depending on the voltage value detected by the power supply voltage detecting part 51 makes it possible to avoid the stop of the charging due to the voltage drop immediately after the start of the charging and continue subsequent charging of the battery 43.

Also, during the certain time after the start of the charging, since the maximum current value not causing the voltage drop exceeding the voltage variation range can be set as the charging current value by increasing the charging current value set for the charging circuit 42 stepwise or at a predetermined gradient, it becomes possible to efficiently charge the battery 43 in a limited charging environment.

In addition, in the X-ray imaging apparatus for rounds according to the present invention, the battery 43 is charged at a different charging current value depending on the variation in the voltage of the external power supply 41. For this reason, it may be adapted to display a charge indicator on the touch panel 18 so as to be able to notify which level of charging current the charging is performed at.

REFERENCE SIGNS LIST

11 Cart
12 Support post
13 Arm
16 Rear wheel
17 Front wheel
18 Touch panel
21 X-ray tube
22 Collimator
23 X-ray detector
24 Handle
30 Holding part
41 External power supply
42 Charging circuit
43 Battery
44 X-ray high-voltage control device
45 Motor driving part
46 Motor
50 Control circuit
51 Power supply voltage detecting part
52 Charged voltage detecting part
53 Charging current detecting part
54 Charging current value control part

The invention claimed is:

1. An X-ray imaging apparatus for rounds, comprising: an apparatus main body mounted with a battery; an X-ray tube supported by the apparatus main body via a supporting member; and an X-ray detector configured to detect an X-ray that has been emitted from the X-ray tube and passed through a subject, wherein the battery serves as a power supply, the apparatus further comprising:
    a charging circuit configured to control charging current to reach a setting value of charging current for the battery,
    a control circuit having:
    a voltage detecting part configured to detect a power supply voltage that is inputted from an external power supply to the charging circuit when charging the battery; and
    a charging current control part configured to, during a certain time after a start of the charging of the battery, adjust the setting value of charging current for the battery so that the power supply voltage stays within an allowable voltage variation range.

2. The X-ray imaging apparatus for rounds, according to claim 1, wherein the charging current control part increases the setting value of the charging current in one of a multistep manner or at a predetermined gradient during the certain time after the start of the charging of the battery.

* * * * *